United States Patent [19]

Cheng et al.

[11] Patent Number: 4,746,515

[45] Date of Patent: May 24, 1988

[54] SKIN PERMEATION ENHANCER COMPOSITIONS USING GLYCEROL MONOLAURATE

[75] Inventors: Yu-Ling Cheng, Cupertino; Diane E. Nedberge, Los Altos; Edna Sugihara, Mountain View, all of Calif.

[73] Assignee: ALZA Corporation, Palo Alto, Calif.

[21] Appl. No.: 19,470

[22] Filed: Feb. 26, 1987

[51] Int. Cl.[4] ............................................. A61F 13/00
[52] U.S. Cl. .................................... 424/449; 424/448; 514/946
[58] Field of Search ................ 424/448, 449; 514/946, 514/947

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,568,343 | 2/1986 | Leeper et al. | 604/896 |

FOREIGN PATENT DOCUMENTS 1001949 8/1965 Fed. Rep. of Germany .

OTHER PUBLICATIONS

Idson, B., "Percutaneous Adsorption", Journal of Pharmaceutical Sciences, vol. 64, No. 6 (Jun. 1975), pp. 901-924.

Primary Examiner—Thurman K. Page
Assistant Examiner—L. R. Horne
Attorney, Agent, or Firm—Shelley G. Precivale; Edward L. Mandell; Paul L. Sabatine

[57] ABSTRACT

A method for enhancing the transdermal flux of a transdermally deliverable drug through intact skin is described in which the drug is delivered simultaneously with glycerol monolaurate. Preferred embodiments of therapeutic systems for delivering drug and glycerol monolaurate employ matrix containing drug at a concentration above saturation.

13 Claims, 1 Drawing Sheet

SKIN PERMEATION ENHANCER COMPOSITIONS USING GLYCEROL MONOLAURATE

FIELD OF THE INVENTION

This invention relates to the transdermal delivery of drugs or other biologically active agents and more particularly to novel methods and compositions for enhancing the permeability of skin or other body surfaces to biologically active agents.

RELATED PATENT APPLICATIONS

This invention is related to the inventions disclosed in the copending, coassigned patent applications of Gale, et al for Transdermal Administration of Progesterone, Estradiol Esters and Mixtures Thereof, of Cheng, et al for Skin Permeation Enhancer Compositions using Sucrose Esters, and of Nedberge, et al for Transdermal Contraceptive Formulations, all of like date herewith.

BACKGROUND OF THE INVENTION

The transdermal route of parental delivery of drugs provides many advantages and transdermal systems for delivering a wide variety of drugs or other beneficial agents are described in U.S. Pat. Nos. 3,598,122, 3,598,123, 4,379,454, 4,286,592, 4,314,557 and 4,568,343, for example, all of which are incorporated herein by reference. In many cases, drugs which would appear to be ideal candidates for transdermal delivery are found to have such low permeability through intact skin that they cannot be delivered at therapeutically effective rates from reasonably sized systems. In an effort to increase skin permeability it has been proposed to concurrently deliver the drug in the presence of a permeation enhancer. Various materials have been suggested for this purpose as described in U.S. Pat. Nos. 4,299,826, 4,343,798, 4,046,886, 4,130,643, 4,405,616, 4,335,115, 4,130,667, 3,903,256, 4,379,454, 3,527,864, 3,952,099, 3,896,238, 3,472,931 all of which are incorporated herein by reference, British Pat. No. 1,001,949 and Idson, Percutaneous Absorption, J. Phar. Sci., Vol. 64, No. b6, June 1975, pp. 901-924 (particularly 919-921). To be considered useful a permeation enhancer should possess certain characteristics in addition to its ability to enhance the permeability of at least one and preferably a large number of drugs. These characteristics include being non-toxic, non-irritating on prolonged exposure and under occlusion, and non-sensitizing on repeated exposure. Preferaly it should also be odorless and capable of delivering drugs without producing burning or tingling sensations.

According to our invention, we have discovered that surfactants and in particular glycerol monolaurate (GML), are effective in enhancing the permeation of a large number of drugs and other therapeutic or beneficial agents through body surfaces and membranes, generally, and skin, particularly, and when formulated in pharmaceutical compositions with other materials appears to satisfy the criteria noted above.

It is accordingly an object of our invention to increase the skin permeability of humans to the transport of drugs and other beneficial agents by the concurrent applications of the drug or beneficial agent and GML to the body surface.

It is another object of our invention to provide compositions of matter for application to the skin which comprise GML and a transdermally deliverable drug or beneficial agent.

It is another object of our invention to provide transdermal therapeutic systems for the concurrent delivery of GML and a drug or beneficial agent.

These and other objects and advantages will be readily apparent from the following decription with reference to the accompanying drawings wherein:

DESCRIPTION OF THE INVENTION

Figure 1:
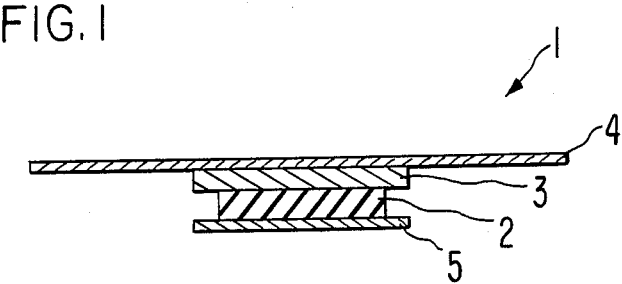
FIG. 1 is a cross-sectional, perspective view through one embodiment of the transdermal therapeutic system according to this invention.

According to our invention we have discovered that GML can be used to enhance the permeability to drugs and other beneficial agents of skin generally and, more particularly, to enhance the transdermal permeability of a multiplicity of drugs useful in the treatment of a wide variety of conditions and indications. As used herein the term "drug" relates to a biologically active agent, compound or composition of matter which is administered for the purpose of providing some beneficial or therapeutic effect. As used herein the term "transdermal" delivery relates to the delivery of a drug by passage through intact skin into the vascularized layers below the stratum corneum for absorption by the blood stream. Thus transdermal delivery is distinguished from topical application to the surface of intact skin for topical treatment or to application to open wounds or to skin lacking the stratum corneum such as burned or abraded skin.

According to our invention GML and the biologically active agent (drug) to be delivered are placed in drug and GML transmitting relationship to the skin, preferably in a carrier therefor, and maintained in place for the desired period of time. The drug and GML are typically dispersed within a physiologically compatible matrix or carrier as more fully described below which may be applied directly to the body as an ointment, gel, cream, suppository or sublingual or buccal tablet for example but are more preferably administered from a transdermal therapeutic system as more fully described below.

We have also found that GML, in addition to its known low toxicity and colorless and odorless nature, does not sensitize skin on repeated exposure. Further, it can be applied to the skin in compositions that do not produce irritation even on occulsion and repeated application to the same site and is capable of enhancing drug flux without producing objectionable skin sensations.

GML has utility in connection with the delivery of drugs within the broad class normally delivered through skin. In general, this includes therapeutic agents in all of the major therapeutic areas including, but not limited to, anti-infectives, such as antibiotics and antiviral agents, analgesics and analgesic combinations, anthemidines, antiarthritics, antiasthmatic agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrythmics, antihypertensives, diuretics, vasodilators including general, coronary, peripheral and cerebral, central nervous system stimulants, cough and cold preparations, decongestants, hormones, hypnotics, immunosuppressives, muscle relaxants, parasympatholytics, parasympathomimetics, pyschostimulants, sedatives and tranquilizers.

We have demonstrated the utility of GML as a permeation enhancer for a large number of dissimilar drugs within some of these classes and believes it to be applicable to an even larger number of such drugs including, by way of example and not for purposes of limitation: scopolamine, isosorbide dinitrate, nitroglycerin, estradiol, clonidine, cortisone, hydrocortisone, theophylline, phenylephrine, terbutaline, ephedrine, narcotine, quinidine, estradiol diacetate, progesterone, pilocarpine, furosemide, tetracycline, insulin, chlorpheniramine, sulfathiazides, propanolol, testosterone, norgestrel, lidocaine, morphinone, morphine, dihydrocodeine, dihydromorphine, oxycodone, hydrocodone, codeine, norcodeine, hydromorphine, normophine, norlevorphanol, dihydrothebaine, ouabain, bromocyrptine, haloperidol, guanabenz, salbutamol, oxprenolol, tetracaine, dibucaine, altenolol, pindolol, and timolol, for example as well as to other drugs not specifically noted herein.

The effect of GML as a permeation enhancer for other drugs not specifically set forth herein, may be readily determined by a worker skilled in the art from in vitro permeation meaurements performed on cadaver skins or other membranes in conventional diffusion cell tests as well as by in vivo measurements of blood or urine levels for example.

GML has a permeation enhancing effect on the transport of drugs through body surface tissues generally in addition to the skin. Nevertheless, because skin is one of the most effective of the body's barriers to permeation of foreign substances, the effect of GML on skin permeation makes it extremely useful in transdermal drug delivery. The following description of preferred embodiments of the invention is therefore directed primarily to improving transdermal delivery of drugs.

Referring now to FIG. 1, a transdermal therapeutic system 1 according to this invention is shown which comprises a drug/permeation enhancer reservoir 2 in the form of a matrix containing the drug and GML. The reservoir 2 is covered by an impermeable backing 3 which is preferably sized slightly larger in circumference than reservoir 2. Means 4 for maintaining the syste on the skin may either be fabricated together with or provided separately from the remaining elements of the system which means in the embodiment of FIG. 1 takes the form of an adhesive overlay. An adhesive overlay is used with this invention because GML adversely affects the adhesive properties of most pharmaceutically acceptable contact adhesives. For this reason, impermeable backing layer 3 is preferably sized slightly larger than the reservoir 2 to provide a peripheral area around reservoir 2 free of GML to prevent adverse interaction between the adhesive in the overlay 4 and any of the GML which may seep from under the base of reservoir 2 in use. A strippable release liner 5, adapted to be removed prior to application would normally be included in the packaged product. Various materials suited for the fabrication of the various layers are disclosed in the aforementioned patents. The composition of the matrix may, depending on the drug to be delivered, be either aqueous based or anydrous and suitable matrices or carriers described in the above identified patents. Suitable matrix materials include, without limitation, natural and synthetic rubbers such as polbutylene, polyisobutylene, polybutadiene, polyethylene, styrenebutadine, copolymers, polyisoprene, polyurethane, ethylene/propylene copolymers, polyalkylacrylate polymers, copolyesters, ethylene/acrylic copolymers, silicones and butadiene/acrylonitrile copolymers for example and other polymers such as the ethylene vinylacetate (EVA) polymers described in U.S. Pat. No. 4,144,317 (which is incorporated herein by reference), for example, gelled or thickened mineral oil, petroleum jelly and various aqueous gels and hydrophilic polymers. Typically the drug is dispersed through the matrix or carrier at a concentration in excess of saturation, the amount of the excess being a function of the intended useful life of the system. The drug, however, may be present at initial levels below saturation without departing from this invention. The GML is preferably dispersed through the matrix at a concentration sufficient to provide permeation enhancing concentrations of GML in the reservoir throughout the anticipated administration time.

In addition to the drug and GML, which are essential to the invention, the matrix may also contain other materials such as dyes, pigments, inert fillers or other permeation enhancers, excipients, and conventional components of pharmaceutical products or transdermal therapeutic systems as known to the art.

Figure 2:
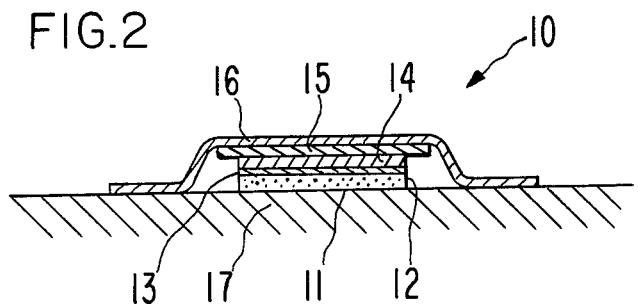
FIG. 2 is cross-sectional view through another embodiment of the transdermal therapeutic system according to this invention.

Referring now to FIG. 2 another embodiment of this invention is shown in place upon the skin 17 of a patient. In this embodiment the transdermal therapeutic system 10 comprises a multilaminate drug/enhancer reservoir 11 having at least two zones 12 and 14. Zone 12 consists of a drug reservoir substantially as described with respect to FIG. 1. Zone 14 comprises a GML reservoir which is preferably made from, but not limited to, substantially the same matrix as used to form zone 12 and which is substantially free of any undissolved drug. A rate-controlling membrane 13 for controlling the release rate of GML from zone 12 to the skin may also be utilized between zones 12 and 14 if desired. Suitable rate-controlling membranes may be formed from polymers having a permeability to GML lower than that of zone 12. Alternately, membrane 13 may control the release rate of both the permeation enhancer and the drug. In that case, zone 14 would contain both the drug and the permeation enhancer reserves.

An advantage of the system described in FIG. 2 is that the drug loaded zone 12 is concentrated at the skin surface rather than throughout the entire mass of the reservoir. This functions to reduce the amount of drug in the system while maintaining an adequate GML supply.

Superimposed over the drug/enhancer reservoir 11 is an impermeable backing 15 and adhesive overlay 16 as described above with respect to FIG. 1. In addition, a strippable release liner (not shown) would preferably be provided on the system prior to use as described with respect to FIG. 1 and removed prior to application to the skin 17.

With both FIGS. 1 and 2, the adhesive overlays can be eliminated if the skin contacting layer can be made adhesive. Use of such an in-line contact adhesive would mainly be limited by the compatability of the adhesive with the GML component of the drug delivery system.

In the embodiments of FIGS. 1 and 2 the carrier or matrix material has sufficient viscosity to maintain its shape without oozing or flowing. If the matrix or carrier is a low viscosity flowable material, the composition can be fully enclosed in a pouch or pocket between the impermeable backing and a permeable or microporous skin contacting membrane as known to the art from U.S. Pat. No. 4,379,454, noted above, for example. Although the invention is most useful with drugs whose permeability is too low for therapeutic effects to be obtained in the absence of an enhancer; its use with systems employing drug rate controlling membranes such as disclosed in U.S. Pat. Nos. 3,598,122 and 3,598,123 noted above is also contemplated.

EXAMPLE I

A transdermal therapeutic system as described with respect to FIG. 1 for administration of progesterone was formulated from progesterone (10%), GML, EVA 40 and Staybelite Ester #5 (Hercules, Inc.). This system was tested on a human subject by application of an 80 $cm^2$ patch on the upper outer arm. A similar system for the administration of estradiol was formulated from estradiol valerate (10%), GML, EVA 40 and Staybelite Ester #5 and simultaneously tested by application of an 80 $cm^2$ patch on the chest of the aforementioned human subject.

Measurement of the plasma progesterone and estradiol levels after a 24 hour period indicated an increase in progesterone of 70 ng/dl and an increase in estradiol of 4.7 ng/dl.

EXAMPLE II

The following table provides in vitro progesterone skin flux data for various formulations. Comparisons are made with other permeation enhancers: glycerol monooleate (GMO) and sucrose monococoate (SMC) sucrose recinoleate (SR) and polyethylene glycol (PEG 40) with castor oil.

TABLE I

| FORMULATION, weight percent | PROGESTERONE SKIN FLUX, $\mu g/cm^2/hr$ |
| --- | --- |
| 24.2% GML, 5.8% Progesterone, 38.8% EVA 40, 31.2% Staybelite Ester #5 | 2.26 |
| 25.2% GML, 10.0% Progesterone, 35.9% EVA 40, 28.9% Staybelite Ester #5 | 3.19 |
| 2.5% Progesterone, 97.5% EVA 51 | 0.14 |
| 25.0 GMO, 10.0% Progesterone, 36.0% EVA 40, 29.0% Staybelite Ester #5 | 2.38 |
| 25.5% SMC, 10.0% Progesterone, 35.8% EVA 40, 28.7% Staybelite Ester #5 | 2.33 |
| 25.5% SR, 8% Progesterone, 39.1% EVA 40, 27.4% Staybelite Ester #5 | 1.01 |
| 25.4% PEG 40 Castor Oil, 8% Progesterone, 39.1% EVA 40, 27.5% Staybelite Ester #5 | 0.75 |
| 25.0% GML, 10% Progesterone, 35.9% EVA 40, 28.9% Staybelite Ester #5 | 3.08 |

Having thus generally described our invention and having provided specific embodiments thereof it will be readily apparent to workers skilled in the art that various modifications and substitutions can be made without departing from the scope of this invention which is limited only to the following claims.

We claim:

1. A composition of matter for application to a body surface or membrane to deliver a biologically active agent by permeation through a body surface or membrane comprising, in combination: a biologically active agent and a permeation enhancing amount of glycerol monolaurate whereas said agent and glycerol monolaurate are dispersed within a carrier.

2. The composition of claim 1 wherein said agent is present in an amount in excess of its saturation concentration in the carrier.

3. The composition of claim 1 wherein said body surface or membrane is intact skin.

4. A transdermal therapeutic system comprising a combination of matter for application to a body surface or membrane comprising a biologically active agent and a permeation enhancing amount of glycerol monolaurate, in combination with:
   (a) an occlusive backing behind the skin distal surface of said composition, and
   (b) means for maintaining said composition in agent and glycerol monolaurate transferring relationship to intact skin.

5. A method for enhancing the flux of a biologically active agent through a body surface or membrane which comprises placing a source of said agent in agent transmitting relationship to said surface or membrane in the presence of a permeation enhancing amount of glycerol monolaurate wherein said agent and glycerol monolaurate are dispersed within a carrier.

6. The method of claim 5 wherein the source of said agent contains agent in excess of its saturation concentration in said source.

7. The method of claim 5 wherein said body surface or membrane is intact skin.

8. In a method for administering a biologically active agent by permeation through an intact body surface which comprises:
   (a) placing a source of said agent and a permeation enhancer therefor in agent and permeation enhancer transmitting relationship to said body surface, and
   (b) maintaining said source in contact with said body surface for a period of time sufficient to produce a beneficial effect; the improvements wherein said permeation enhancer is glycerol monolaurate wherein said agent and permeation enhancer are dispersed within a carrier.

9. The method of claim 8 wherein said body surface is the skin.

10. In a transdermal therapeutic system comprising;
   (a) a source of a transdermally deliverable biologically active agent,
   (b) a source of skin permeation enhancer for said agent and
   (c) means for maintaining said system in agent and permeation enhancer transferring relationship to intact skin; the improvement wherein said permeation enhancer is glycerol monolaurate.

11. The system of claim 10 wherein said agent is present in said source at a concentration above saturation.

12. The system of claim 10 wherein said agent is present at a concentration sufficient to maintain the concentration above saturation for an extended period of time and said glycerol monolaurate is present at a concentration sufficient to provide permeation enhancement throughout said extended period of time.

13. A composition of matter for application to a body surface or membrane to deliver a biologically active agent by permeation through a body surface or membrane comprising, in combination: progesterone as said agent and a permeation enhancing amount of glycerol monolaurate wherein said agent and glycerol monolaurate are dispersed within a carrier.

* * * * *